(12) United States Patent
Mori et al.

(10) Patent No.: US 10,765,640 B2
(45) Date of Patent: *Sep. 8, 2020

(54) NON-AQUEOUS PATCH

(75) Inventors: Tatsuya Mori, Saga (JP); Naoyuki Saida, Saga (JP)

(73) Assignees: ITOCHU CHEMICAL FRONTIER Corporation, Tokyo (JP); OISHI KOSEIDO CO., LTD., Saga (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/346,794

(22) PCT Filed: Sep. 27, 2011

(86) PCT No.: PCT/JP2011/072072
§ 371 (c)(1),
(2), (4) Date: Jul. 1, 2014

(87) PCT Pub. No.: WO2013/046335
PCT Pub. Date: Apr. 4, 2013

(65) Prior Publication Data
US 2014/0356412 A1  Dec. 4, 2014

(51) Int. Cl.
*A61K 9/70* (2006.01)
*A61K 31/167* (2006.01)

(52) U.S. Cl.
CPC .......... *A61K 9/7038* (2013.01); *A61K 9/7053* (2013.01); *A61K 31/167* (2013.01)

(58) Field of Classification Search
None
See application file for complete search history.

(56) References Cited

U.S. PATENT DOCUMENTS

| | | |
|---|---|---|
| 4,685,907 A | 8/1987 | Agren et al. |
| 4,946,853 A | 8/1990 | Bannan et al. |
| 5,098,417 A | 3/1992 | Yamazaki et al. |
| 5,234,957 A | 6/1993 | Mantelle |
| 5,411,738 A | 5/1995 | Hind |
| 5,478,567 A | 12/1995 | Nakagawa et al. |
| 5,527,536 A | 6/1996 | Merkle et al. |
| 5,536,263 A | 7/1996 | Rolf et al. |
| 5,589,180 A | 12/1996 | Hind |
| 5,601,838 A | 2/1997 | Hind |
| 5,601,839 A | 2/1997 | Quan et al. |
| 5,618,274 A | 4/1997 | Rosenthal |
| 5,709,869 A | 1/1998 | Hind |
| 5,741,510 A | 4/1998 | Rolf et al. |
| 5,773,022 A | 6/1998 | Nyqvist-Mayer et al. |
| 5,804,213 A | 9/1998 | Rolf |
| 5,827,529 A | 10/1998 | Ono et al. |
| 5,830,497 A | 11/1998 | Yamanaka et al. |
| 5,834,010 A | 11/1998 | Quan et al. |
| 5,891,919 A | 4/1999 | Blum et al. |
| 5,979,447 A | 11/1999 | Al-Falahe |
| 5,985,317 A | 11/1999 | Venkateshwaran et al. |
| 6,096,333 A | 8/2000 | Rolf et al. |
| 6,096,334 A | 8/2000 | Rolf |
| 6,120,792 A | 9/2000 | Juni |
| 6,211,425 B1 | 4/2001 | Takayasu et al. |
| 6,221,383 B1 | 4/2001 | Miranda et al. |
| 6,251,100 B1 | 6/2001 | Flock et al. |
| 6,255,502 B1 | 7/2001 | Penkler et al. |
| 6,264,927 B1 | 7/2001 | Monahan |
| 6,264,981 B1 | 7/2001 | Zhang et al. |
| 6,297,290 B2 | 10/2001 | Guise et al. |
| 6,299,902 B1 | 10/2001 | Jun et al. |
| 6,361,709 B1 | 3/2002 | Rolf et al. |
| 6,361,790 B1 | 3/2002 | Rolf et al. |
| 6,365,178 B1 | 4/2002 | Venkatesharen et al. |
| 6,383,511 B1 | 5/2002 | Cassel |
| 6,410,048 B1 | 6/2002 | Fotinos |
| 6,455,066 B1 | 9/2002 | Fischer et al. |
| 6,461,644 B1 | 10/2002 | Jackson et al. |
| 6,469,227 B1 | 10/2002 | Cooke et al. |
| 6,528,086 B2 | 3/2003 | Zhang |

(Continued)

FOREIGN PATENT DOCUMENTS

| | | |
|---|---|---|
| EP | 2311498 | 4/2001 |
| EP | 1125578 A1 | 8/2001 |

(Continued)

OTHER PUBLICATIONS

Grunenthal Ltd., Versatis 5% Medicated Plaster, 2015.
Stahl, Jessica et al., BMC Veterinary Research, the effects of chemical and physical penetration enhancers on the percutaneous permeation of lidocaine through equine skin, 2014, pp. 2-6, 10:138.
International Search Report and Written Opinion for PCT/JP2011/060781 dated Jun. 14, 2011, 10 pages.
International Search Report and Written Opinion for PCT/JP2011/072072 dated Oct. 25, 2011, 14 pages.
International Search Report and Written Opinion for PCT/JP2016/075376 dated Nov. 29, 2016, 8 pages.
Extended European Search Report dated Oct. 22, 2014 for EP Application No. 11865320.3 filed May 10, 2011, 7 pages.

(Continued)

*Primary Examiner* — Robert T. Crow
*Assistant Examiner* — John P Nguyen
(74) *Attorney, Agent, or Firm* — Cooley LLP

(57) ABSTRACT

[Problem]
If lidocaine is composed of non-aqueous patch, the adhesive power of the preparation tends to get lower, as the composition amount of lidocaine is higher. It is popular to solve lidocaine in dissolving agent in order to compose lidocaine in patch and release effective amount into skin. However, if the amount of dissolving agent gets higher, the adhesive power gets extremely lower, so that an long-time attachment is difficult.

[Solution]
A non-aqueous patch comprising lidocaine and/or its reactant, and a dissolving agent which are contained in a base of plaster, the plaster being hold by a support, of which strength of 50% stretched to longitudinal direction is less than 2,000 g/50 mm and of biaxially-oriented stretch cloth.

8 Claims, 1 Drawing Sheet

(56) References Cited

U.S. PATENT DOCUMENTS

| | | |
|---|---|---|
| 6,546,281 B1 | 4/2003 | Zhang |
| 6,562,363 B1 | 5/2003 | Mantelle et al. |
| 6,580,011 B1 | 7/2003 | Jennings-Spring |
| 6,645,521 B2 | 11/2003 | Cassel |
| 6,689,380 B1 | 2/2004 | Marchitto et al. |
| 6,746,689 B2 | 6/2004 | Fischer et al. |
| 6,825,203 B2 | 11/2004 | Pasternack et al. |
| 6,830,758 B2 | 12/2004 | Nichols et al. |
| 6,953,590 B1 | 10/2005 | Owaki et al. |
| 6,995,819 B2 | 2/2006 | Kaneko et al. |
| 6,998,109 B1 | 2/2006 | Pearson et al. |
| 7,094,228 B2 | 8/2006 | Zhang et al. |
| 7,127,285 B2 | 10/2006 | Henley et al. |
| 7,166,641 B2 | 1/2007 | Lee et al. |
| 7,179,477 B2 | 2/2007 | Gupta |
| 7,288,265 B1 | 10/2007 | Rolf |
| 7,655,038 B2 | 2/2010 | Luthra et al. |
| 7,655,687 B2 | 2/2010 | Hamamoto et al. |
| 7,695,733 B2 | 4/2010 | Zasler et al. |
| 7,728,188 B2 | 6/2010 | Tippett |
| 7,754,240 B2 | 7/2010 | Staniforth et al. |
| 7,829,099 B2 | 11/2010 | Woeller et al. |
| 7,904,146 B2 | 3/2011 | Anderson et al. |
| 7,910,135 B2 | 3/2011 | St John et al. |
| 7,921,999 B1 | 4/2011 | Kimball |
| 7,993,654 B2 | 8/2011 | Woeller et al. |
| 8,231,906 B2 | 7/2012 | Mantelle |
| 8,722,065 B2 | 5/2014 | Ishibashi et al. |
| 9,283,174 B2 | 3/2016 | Mori et al. |
| 9,925,264 B2 | 3/2018 | Mori et al. |
| 9,931,403 B2 | 4/2018 | Mori et al. |
| 2002/0045043 A1* | 4/2002 | Kuniya ............... C09J 121/00 428/343 |
| 2002/0106402 A1* | 8/2002 | Hartwig .............. A61K 9/0014 424/449 |
| 2003/0109818 A1 | 6/2003 | Tsrudu et al. |
| 2003/0124174 A1 | 7/2003 | Galer |
| 2005/0042269 A1* | 2/2005 | Tateishi ................ A61F 13/02 424/449 |
| 2005/0260255 A1* | 11/2005 | Terahara et al. ............ 424/449 |
| 2006/0029654 A1* | 2/2006 | Cassel ................. A61K 9/7061 424/449 |
| 2007/0196458 A1* | 8/2007 | Zhang ................. A61K 9/0014 424/448 |
| 2009/0004255 A1* | 1/2009 | Uchida ................ A61K 9/7053 424/447 |
| 2009/0297591 A1 | 12/2009 | Chiang et al. |
| 2009/0305068 A1* | 12/2009 | Morishita ................. C09J 9/02 428/483 |
| 2010/0003313 A1 | 1/2010 | Suzuki et al. |
| 2010/0029704 A1 | 2/2010 | Hanma et al. |
| 2010/0092544 A1 | 4/2010 | Okada et al. |
| 2010/0234471 A1 | 7/2010 | Ishibashi et al. |
| 2011/0097384 A1 | 4/2011 | Kanios et al. |
| 2011/0152377 A1 | 6/2011 | Hanma et al. |
| 2012/0071511 A1 | 3/2012 | Naruse et al. |
| 2012/0171278 A1 | 7/2012 | Takada et al. |
| 2012/0184563 A1 | 7/2012 | Hanma |
| 2012/0283671 A1 | 11/2012 | Shibata et al. |
| 2014/0171509 A1* | 6/2014 | Mori et al. ..................... 514/626 |
| 2016/0184432 A1 | 6/2016 | Mori et al. |
| 2018/0177742 A1 | 6/2018 | Mori et al. |
| 2018/0256495 A1 | 9/2018 | Hanma et al. |
| 2018/0326068 A1 | 11/2018 | Mori et al. |

FOREIGN PATENT DOCUMENTS

| | | |
|---|---|---|
| EP | 1238664 A1 * | 9/2002 |
| EP | 1293199 A1 | 3/2003 |
| EP | 2210599 | 7/2010 |
| EP | 2708229 A1 | 3/2014 |
| JP | H07215850 A | 8/1995 |
| JP | 9-315964 | 12/1997 |
| JP | 09-315964 | 12/1997 |
| JP | 10-147521 | 6/1998 |
| JP | 2816765 B2 | 10/1998 |
| JP | 11-049670 | 2/1999 |
| JP | 2000-178186 | 6/2000 |
| JP | 2001-302501 | 10/2001 |
| JP | 2003-191659 A | 7/2003 |
| JP | 2009120551 | 6/2009 |
| JP | 2009524586 | 7/2009 |
| JP | 2010-202663 A | 9/2010 |
| JP | 2011-521975 A | 7/2011 |
| JP | 2013513852 | 4/2013 |
| JP | 5856153 B2 | 2/2016 |
| WO | 1992015289 | 9/1992 |
| WO | WO-1999/015210 A2 | 4/1999 |
| WO | WO 2007/070679 | 6/2007 |
| WO | 2009060629 A1 | 5/2009 |
| WO | 2010016219 A1 | 2/2010 |
| WO | WO-2012/153396 A1 | 11/2012 |
| WO | WO-2013/046335 A1 | 4/2013 |
| WO | WO-2017/034041 A1 | 3/2017 |
| WO | WO-2019/220420 A1 | 11/2019 |

OTHER PUBLICATIONS

Extended European Search Report dated Sep. 14, 2015 for EP Application No. 11873101.7 filed Sep. 27, 2011, 6 pages.

Extended European Search Report dated Jun. 18, 2018 for EP Application No. 18166768.4 filed Sep. 27, 2011, 7 pages.

Final Office Action dated May 22, 2019 for U.S. Appl. No. 15/891,915, filed Feb. 8, 2018, 13 pages.

Final Office Action dated May 1, 2019 for U.S. Appl. No. 15/904,071, filed Feb. 23, 2018, 9 pages.

Haghpanah, S. et al. "Application No. 207962orig1s000 Summary Review", Clinical Review, Cross-Discipline Team Leader, and Summary Division Director Review, NDA 207962 ZTlido Patch Complete Response Submission; Ref. ID: 4227523: 1-38. (Feb. 28, 2018) [retrieved on Nov. 15, 2019]. Retrieved from the Internet <https://www.accessdata.fda.gov/drugsatfda_docs/nda/2018/207962Orig1s000SumR.pdf>.

Hoffman, M. "FDA Approves Lidocaine Patch 1.8% for Post-Herpetic Neuralgia", MD Mag: 2 pages. (Feb. 28, 2018) [retrieved on Nov. 15, 2019]. Retrieved from the Internet <https://www.mdmag.com/medical-news/fda-approves-lidocaine-patch-18-for-postherpetic-nerualgia>.

Schriever, J. "Patch adhesion and local tolerability of Transdermal Delivery Systems Requirements according to the new draft EMA Guidelines", BfArM Federal Institute for Drugs and Medical Devices: 20 pages. (May 16, 2013) [retrieved on Nov. 15, 2019]. Retrieved from the Internet <https://www.agah.eu/wp-content/uploads/Schriever_patch_adhesion_local_tolerability.pdf>.

International Search Report and Written Opinion for PCT/IB2019/054155 dated Oct. 15, 2019, 14 pages.

Extended European Search Report dated Oct. 21, 2019 for EP Application No. 19180829.4 filed May 10, 2011, 8 pages.

Inada, T., et al. "Lidocaine tape relieves pain due to needle insertion during stellate ganglion block", Canadian Journal of Anaesthesia 44(3):259-62. (Apr. 1997).

Non-Final Office Action dated Dec. 18, 2019 for U.S. Appl. No. 15/891,915, filed Feb. 8, 2018, 7 pages.

Bica, Katharina et al., Liquid forms of pharmaceutical co-crystals: exploring the boundaries of salt formation, The Royal Society of Chemistry, Chem Commun., 2011, 2267-2269, 47.

Endo Pharmaceuticals Inc., Lidoderm—lidocaine patch, 2015.

* cited by examiner

| drug remaining ratio | 0 | 4 | 8 | 12 |
|---:|---:|---:|---:|---:|
| Example1 | 100 | 76.5 | 68.2 | 64.9 |
| Example2 | 100 | 83.2 | 72.7 | 70.2 |
| Example3 | 100 | 85.9 | 74.7 | 73.5 |
| Example4 | 100 | 89.4 | 83.7 | 79.1 |
| Comparative Example1 | 100 | 97.9 | 97.6 | 97.5 |
| Comparative Example2 | 100 | 98.3 | 96.3 | 96.1 |
| Comparative Example3 | 100 | 96.7 | 96.3 | 96.7 |
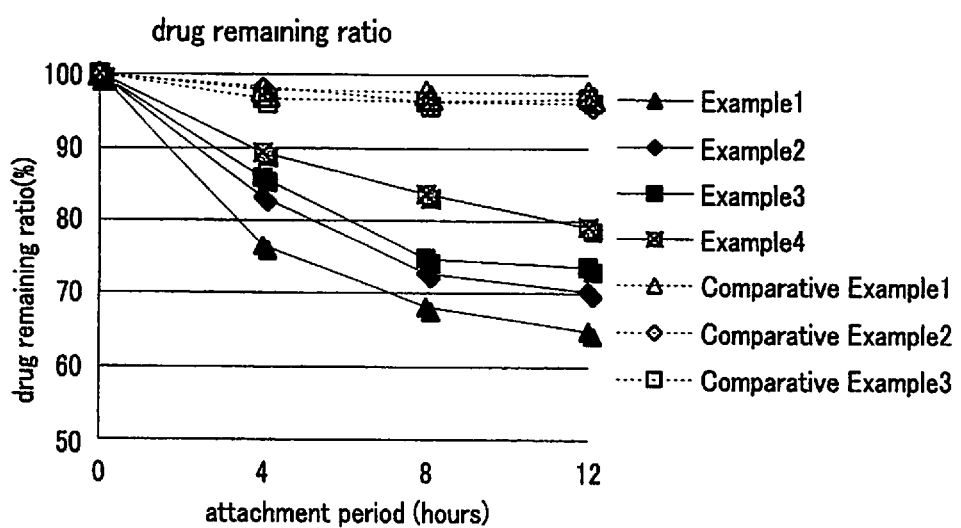

NON-AQUEOUS PATCH

CROSS REFERENCE TO RELATED APPLICATIONS

This application is a U.S. National Phase application under 35 U.S.C. § 371 of International Application No. PCT/JP2011/072072, filed on Sep. 27, 2011, which designated the United States.

TECHNICAL FIELD

The present invention relates to a non-aqueous patch for medical and home use using lidocaine.

BACKGROUND ART

Lidocaine is used for the purpose of local anesthesia or topical anesthesia. The usage form of lidocaine is an external preparation comprising lidocaine or a patch comprising lidocaine. Examples of external preparations include ointment, cream, jelly, spray, etc., which are used, for example, for topical anesthesia of the skin in the treatment of postherpetic neuralgia. Examples of patches include aqueous base patches (cataplasms) and non-aqueous patches (tapes).

An example of aqueous base patches is Lidoderm (registered trademark of Endo Pharmaceuticals (U.S.)), which is mainly used for topical anesthesia of the skin in the treatment of postherpetic neuralgia, and is also used to relieve pain in various muscles. Aqueous base patches have thick plasters because they contain moisture; therefore, aqueous base patches are poorly compatible with the skin. Moreover, due to very little adhesion, aqueous base patches are difficult to be attached to the skin for a long period of time. Furthermore, the vaporization of moisture problematically causes changes in adhesion and physical properties. Also, Aqueous base patches do not apply to stretchable support, and such aqueous patches are apt to remove after attached to the skin. Therefore, it is difficult to ensure sufficient amount of transpired lidocaine to the skin. Additionally, in order to make lidocaine permeate into the muscle, it is necessary to dissolve lidocaine, and moisture is thus required to dissolve lidocaine.

Next, as a non-aqueous patch, for example, Patent Japanese Patent No. 3159688 (patent Document 1) discloses a technique for alleviating postherpetic neuralgia, in which 5 to 30 wt. % of lidocaine is added as a local anesthetic. Japanese Unexamined Patent Publication No. 7-215850 (Patent Document 2) discloses a technique relating to a percutaneous absorption tape for local anesthesia comprising 5 to 100 wt. % of lidocaine. Japanese Unexamined Patent Publication No. 9-315964 (Patent Document 3) and Japanese Unexamined Patent Publication No. 2001-392501 (Patent Document 4) disclose techniques relating to a patch comprising 0.5 to 5 mass % of lidocaine. WO 2009/060629 (Patent Document 5) discloses a technique relating to a patch comprising 10 to 40 mass % of lidocaine. These non-aqueous patches have poor permeability to the skin because the lidocaine is not dissolved and is present in a crystalline state. In addition, the technique disclosed in Patent Document 5 uses a high concentration of lidocaine.

It is pointed out that lidocaine has an adverse effect on the heart. Prolonged use of a high concentration of lidocaine causes side effects, such as shock, rubor, and irritating sensation. External preparations comprising more than 5 mass % of lidocaine are designated as powerful drugs, and cannot be used as household (nonprescription) medicine.

In contrast, the techniques disclosed in Patent Documents 3 and 4 use a small amount of lidocaine, and can be used for household use; however, even after the small amount of lidocaine is completely dissolved, the lidocaine cannot be stably released over a long period of time (e.g., 12 hours or more) and cannot permeate into the skin. Thus, there is a problem with the pain-relieving effect.

Although it does not refer to lidocaine, Japanese Patent No. 2816765 (Patent document 6) shows an art, using at least one of ketoprofen, Flurbiprofen, loxoprofen, and Ketorolac, as antiphlogistic analgetic, and using polyester cloth of which 50% stretching stress is less than 0.3 kg/cm in average.

CITATION LIST

Patent Literature

[Patent Literature 1] Japanese Patent No. 3159688
[Patent Literature 2] Japanese Unexamined Patent Publication No. 7-215850
[Patent Literature 3] Japanese Unexamined Patent Publication No. 9-315964
[Patent Literature 4] Japanese Unexamined Patent Publication No. 2001-392501
[Patent Literature 5] WO 2009/060629
[Patent Literature 6] Japanese Patent No. 2816765

SUMMARY OF INVENTION

Technical Problem

Aqueous based lidocaine containing preparation has poor adhesive property easy to fall off, and its availability of lidocaine is less than 5% of containing amount of lidocaine. In addition, basic ingredients of lidocaine are easy to be dissolved in organic solvent such as methanol, ethanol, diethyl ether, and the like, and hardly to be dissolved in water.

The art of drug-releasing characteristics of aqueous based patch have not been formulated. In a practical way, it is not considered that what support have preparation, how the patch is ensured to attach stably on a skin, and how to maintain favorable effective ingredient releasing.

If lidocaine is composed of non-aqueous patch, the adhesive power of the preparation tends to get lower, as the composition amount of lidocaine is higher. This is deduced by the following reason: Lidocaine itself have partial compatibility to lipid soluble tackifier resin so that the adhesion property of the tackifier resin gets lowered. It is popular to solve lidocaine in dissolving agent in order to compose lidocaine in patch and release effective amount of lidocaine into skin. However, if the amount of dissolving agent gets higher, the adhesive power gets extremely lower.

The purpose of the present invention is to obtain non-aqueous base, as being used by non-aqueous patch, which can be used in order to relieve muscle pain for long hours. The present invention composed of a small amount of lidocaine, NOT high amount of lidocaine, into plaster, and such small amount of lidocaine is long and stably transferred to muscle by transdermal absorption

Solution to Problem

The present invention is composed of biaxially-oriented stretch cloth as support of non-aqueous patch. After patched to a skin, the patch follows expansion and contraction of the skin so that the patch is unlikely to remove. And also, the present invention regulates some extent of adhesive power so that adhesion to skin is surely and preparation is long and effectively provided by transdermal absorption.

The biaxially-oriented stretch cloth of the present invention is used for support, and its stretch strength to 50% longitudinal extension is less than 2000 g/50 mm (Testing sample size: width 50 mm, length 300 mm, testing length 200 mm, tension rate 500 mm/min)

Appropriate adhesive power, of 180 degree taking off method defined in Z0237 of JIS (Japanese Industrial Standards), of the present invention is from 0.4N/width 25 mm to 5N/width 25 mm. If the adhesive power is higher than 5N/25 mm, a skin may be hurt when the preparation is removed off, and contact dermatitis may be caused by extra tension on a plaster to the skin. If the adhesive power is lower than 0.4N/width 25 mm, the support is easy to remove, especially at the time of skin sweating, so that the preparation of the support cannot be maintained on the skin.

According to mentioned above, it is popular to solve lidocaine in dissolving agent in order to compose lidocaine in patch and release effective amount of lidocaine into skin. However, if the amount of dissolving agent gets higher, the adhesive power gets extremely lower.

Therefore, it is required to select appropriate support such as above-mentioned, and to control adhesive power of preparation.

Appropriate plater materials are selected in regard to compatibility and miscibility to lidocaine.

For example, polyisoprene rubber, polyisobutylene, styrene-isoprene rubber, styrene-butadiene rubber, as rubber based material, can be used. Especially, a combination of polyisoprene and styrene-isoprene-styrene block copolymer may keep plaster appropriate hardness, and the plaster may fit onto a skin.

To the amount of rubber based material, the appropriate amount is from 10 to 50 mass percent in 100 mass percent of plaster, especially from 20 to 40 mass percent is more preferable.

Adhesive power controlling tackifier resin can be composed arbitrary. For example, rosin-based resin, synthetic petroleum resin, terpene resin, phenol resin, alicyclic petroleum resin, and other resins that are generally used in patches. To lidocaine containing non-aqueous patch, terpene resin which has light polarity is a good match, and the preparation does not float off to a skin at the time of sweating on adhesion to the skin, so that it is easy to keep adhesion. The composition amount of said tackifier resin is preferably from 5 to 50 mass percent in 100 mass percent of plaster, and especially from 10 to 40 mass percent is more preferably.

As a softener, polybutene or liquid paraffin may be added. If styrene-isoprene-styrene block copolymer is composed, adding liquid paraffin provides good plaster. The liquid paraffin has compatibility to isoprene groups of styrene-isoprene-styrene block copolymer, and it can make plaster swelling and soft nature so that said plaster have elastic force when applied as a skin patch. The composition amount of liquid paraffin is usually double to composition amount of styrene-isoprene-styrene block copolymer. In general, from one-and-a-half to threefold of composition about of liquid paraffin to composition amount of styrene-isoprene-styrene block copolymer may maintain elastic force of plaster.

As a regulator, anhydrous silicic acid, zinc oxide, or other inorganic substances, zinc stearate, or the like can be used. Especially, anhydrous silicic acid has liquid adsorption capability, so that it is advantageous substance, working as suppression of liquid leaching (lixiviation) and conservation of adhesive power, if liquid substance of dissolving agent is composed. The composition amount of anhydrous silicic acid can work well at the low amount of 0.05 mass % in 100 mass % of plaster. However, anhydrous silicic acid has high specific surface area and low specific gravity. Therefore, the more the composition amount is, cohesive power of plaster gets weak, and adhesive power gets weak. The composition amount of anhydrous silicic acid can work well at high amount of 9 mass % in 100 mass % of plaster. Preferable composition amount of anhydrous silicic acid is from 0.1 to 6 mass % in 100 mass % of plaster.

Lidocaine may be comprised of crystalline state. In such state, a release rate to skin is so lower that the lidocaine preparation cannot be used effectively. Therefore, it is prefer to comprise lidocaine at dissolved state. Effective dissolving agent is composed so that lidocaine or its reactant is included from 0.5 to 7 mass % in plaster. In such manner, lidocaine is completely dissolved, and effective to relieve respective muscle pain for a long time.

As a dissolving agent, organic acid (such as isostearic acid, oleic acid, lactic acid, and the like), fatty acid ester (such as isopropyl myristate, Isostearyl myristate, and the like), polyalcohol (such as dipropylene glycol, polyethylene glycol, glycerin, and the like), and surface acting agent can be used. Especially, combination use of organic acid and polyalcohol (for example, isostearic acid and dipropylene glycol) makes dissolution of lidocaine with fewer composition of dissolving agent, and does not lixiviate (bleed) lidocaine from preparation, so that it contributes to maintain release of lidocaine for a long time. It is considered that negative effect to adhesive force of preparation is inhibited, since water-insoluble higher fatty acid such as isostearic acid (and the like), and water-soluble glycol such as dipropylene glycol (and the like) maintain dissolved state of lidocaine, and maintain mixed state in non-aqueous base material without separation.

As another material, some additive agent may be used. In order to prevent drug to be retrograded, antioxidizing agent such as dibutylhydroxytoluene, and sequestering agent and the like may be used. Also, skin irritant such as menthol and camphor may be added.

As a substrate which retains a plaster mixed of those material, biaxially-oriented stretch cloth is used. Specifically, if the strength of the substrate of preparation patch by 50% longitudinal expansion is less than 2,000 g/50 mm, the patch follows expansion and contraction of the skin. If the strength of the substrate of patch preparation is more than 2,000 g/50 mm, stretchability of the patch is not enough so that the patch is easy to remove from skin when it is attached to the skin.

In addition, it is important to ensure that the adhesive power of the plaster of patch to longitudinal direction is in a range of 0.4N/25 mm width to 5N/25 mm width, by 180 degree adhesive peel strength test which is defined by JIS (Japanese Industrial Standards) No. Z0237. According to the range of adhesive power, the patch is not easy to remove off when a skin moves to a large extent. Therefore, the patch gains long period of time attachability, release of lidocaine is kept in a good extent, and the preparation may be safe product not to damage skin.

Good release of lidocaine means specifically more than 6% of release ratio according to the present invention. The release ratio is calculated on released lidocaine and released ratio of the preparation. The release ratio is actually measured by way of difference between remained amount of lidocaine after 12 hours attachment to a skin and composition amount of lidocaine in the preparation product.

A skin works as barrier to penetration of plaster drug. Respective person has various drug penetration amount each other. Also, the drug penetration amount may vary on an attached part/position. When a design principle of the patch is determined, the skin penetration of drug influences the design significantly. It is preferable rate for effective use of drug to ensure more than 6% release ratio as lidocaine containing patch effective to Muscle pain relieving. There are no need to contain lidocaine at high concentration without reason, and a side effect on high concentration may be avoided. According to such manner, the present invention can provide safe patch effective to muscle pain relieving.

The composition amount of lidocaine is required effective enough to release amount of active ingredient to a skin. According to the present invention, adhesion to a skin for long period of time is ensured so that high amount of lidocaine is not needed and low amount of lidocaine can be of medicinal effect. As above-mentioned, the present invention can avoid a side effect so that it can provide continuous use of drug administration. As a decision branch, it has significant meaning to provide long-time continuous use of drug administration, since muscle pain such as arthritic pain and lumbar pain continue persistent disorder in many cases. As mentioned above, the amount of lidocaine composition is preferably 0.5 to 7.0 mass %, as an amount of sufficient medicinal benefits and insufficient side effect.

As a peeling film covering the plaster surface, a film moderately subjected to a mold release treatment is generally used. Since the drug may be adsorbed to the substrate or peeling film, polyester is generally used as their material.

The mass of the plaster is preferably in the range of 60 to 200 g/m2, and more preferably 80 to 180 g/m2. When the plaster mass is less than 60 g/m2, it is necessary to increase the proportion of lidocaine to the entire plaster, in order to maintain the sufficient efficacy of lidocaine. In this case, however, lidocaine is not sufficiently dissolved and is crystallized; the crystallized lidocaine cannot be efficiently transferred to the skin. Additionally, it is difficult to control the adhesion of the patch, and the plaster is not flexible against the skin and fails to maintain moderate adhesion. In contrast, when the plaster mass is more than 200 g/m2, the plaster is so heavy that plaster dripping easily occurs.

The method of producing the non-aqueous patch of the present invention may be a general method that is conventionally used, such as a hot melt method or a solvent method.

Advantageous Effects of Invention

According to the non-aqueous patch of the present invention, the patch can be kept attached for long period of time, after the patch is attached to a skin, so that release ratio of lidocaine in plaster can be ensured more than 6%. Therefore, if small amount of lidocaine is composed into the plaster, the present invention can provide long-time release of lidocaine to the skin and continuous medicinal effect.

The non-aqueous patch of the present invention is safe and effective patch to relieve respective muscle pain. It can be designed to compose lidocaine at low rate, so that it can avoid abnormal skin penetration on long-time attachment or damaged skin, and rapid increase of blood level.

BRIEF DESCRIPTION OF DRAWINGS

FIG. 1 shows the ratio of the remaining drug.

DESCRIPTION OF EMBODIMENTS

Examples of the present invention are described with reference to Table 1.

Example 1

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 47.6 mass %

Isostearic acid (produced by Kokyu Alcohol Kogyo Co., Ltd.): 0.9 mass %

Dipropylene glycol (produced by NOF Corporation): 0.2 mass %

Lidocaine: 0.5 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the lidocaine, Dipropylene glycol, and Isostearic acid, followed by dissolution at 80° C., was added thereto, and the mixture was mixed under heating at 140° C. until the mixture became homogeneous, thereby obtaining a plaster solution.

The plaster solution was applied to a polyester film treated with silicon so that the plaster weight was 140 g/m². A polyester knitted fabric, of which strength of 50% stretched to longitudinal direction was 1600 g/50 mm, was pasted to the film and cooled. The resultant was then cut into a rectangle (about 14 cm×10 cm).

Example 2

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 45.4 mass %

Isostearic acid (produced by Kokyu Alcohol Kogyo Co., Ltd.): 1.8 mass %

Dipropylene glycol (produced by NOF Corporation): 0.5 mass %

Lidocaine: 1.5 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and lidocaine, followed by dissolution at 80° C., was added thereto, and the mixture was mixed under heating at 140° C. until the mixture became homogeneous, thereby obtaining a plaster solution.

The plaster solution was applied to a polyester film treated with silicon so that the plaster weight was 140 g/m$^2$. A polyester non-woven fabric, of which strength of 50% stretched to longitudinal direction was 1000 g/50 mm, was pasted to the film and cooled. The resultant was then cut into a rectangle (about 14 cm×10 cm).

Example 3

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 44.9 mass %

Isostearic acid (produced by Kokyu Alcohol Kogyo Co., Ltd.): 1.8 mass %

Dipropylene glycol (produced by NOF Corporation): 0.5 mass %

Lidocaine: 2 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and and lidocaine followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 160 g/m$^2$. A polyester non-woven fabric, of which strength of 50% stretched to longitudinal direction was 500 g/50 mm, was pasted to the film and cooled. The resultant was then cut into a rectangle (about 14 cm×10 cm).

Example 4

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 38 mass %

Isostearic acid (produced by Kokyu Alcohol Kogyo Co., Ltd.): 2.5 mass %

Dipropylene glycol (produced by NOF Corporation): 1.5 mass %

Lidocaine: 7 mass %

Light anhydrous silicic acid (trade name "Sylysia 350", produced by Fuji Silysia Chemical Ltd.): 0.7 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and lidocaine, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 160 g/m$^2$. A polyester non-woven fabric, of which strength of 50% stretched to longitudinal direction was 500 g/50 mm, was pasted to the film and cooled. The resultant was then cut into a rectangle (about 14 cm×10 cm).

Comparative Example 1

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 2 mass %

Liquid paraffin (trade name "Hicall", produced by Kaneda Corporation): 63.4 mass %

Isostearic acid (produced by Kokyu Alcohol Kogyo Co., Ltd.): 1.8 mass %

Dipropylene glycol (produced by NOF Corporation): 0.5 mass %

Lidocaine: 1.5 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisoprene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and lidocaine, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m$^2$. A polyester non-woven fabric, of which strength of 50% stretched to longitudinal direction was 3000 g/50 mm, was pasted to the film and cooled. The resultant was then cut into a rectangle (about 14 cm×10 cm).

Comparative Example 2

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 28.2 mass %

Isostearic acid (produced by Kokyu Alcohol Kogyo Co., Ltd.): 12 mass %

Dipropylene glycol (produced by NOF Corporation): 7 mass %

Lidocaine: 2 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and lidocaine, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 140 g/m². A polyester non-woven fabric, of which strength of 50% stretched to longitudinal direction was 3000 g/50 mm, was pasted to the film and cooled. The resultant was then cut into a rectangle (about 14 cm×10 cm).

Comparative Example 3

Styrene-isoprene-styrene block copolymer ("Kraton D1161", produced by Kraton JSR Elastomers K.K.): 20 mass %

Polyisobutylene (trade name "Himol 6H", produced by JX Nippon Oil & Energy Corporation): 10 mass %

Terpene resin (trade name "YS resin 1150N", produced by Yasuhara Chemical Co., Ltd.): 20 mass %

Liquid paraffin (trade name "Hicall", produced by Kaneda Corporation): 44.9 mass %

Isostearic acid (produced by Kokyu Alcohol Kogyo Co., Ltd.): 1.8 mass %

Dipropylene glycol (produced by NOF Corporation): 0.5 mass %

Lidocaine: 2 mass %

Light anhydrous silicic acid (trade name "Sylysia 350", produced by Fuji Silysia Chemical Ltd.): 0.5 mass %

Dibutylhydroxytoluene (trade name "BHT", produced by Honshu Chemical Industry Co., Ltd.): 0.3 mass %

The production method using these materials according to the above formulation was as follows. The styrene-isoprene-styrene block copolymer, polyisobutylene, terpene resin, light anhydrous silicic acid, dibutylhydroxytoluene, and liquid paraffin were placed in a dissolution mixer and dissolved under heating at 150° C. A solution separately prepared by mixing the isostearic acid, dipropylene glycol, and lidocaine, followed by dissolution at 80° C., was added thereto, and the mixture was mixed under heating at 140° C. until the mixture became homogeneous, thereby obtaining a plaster solution. The plaster solution was applied to a polyester film treated with silicon so that the plaster weight was 160 g/m². A polyester non-woven fabric, of which strength of 50% stretched to longitudinal direction was 5000 g/50 mm, was pasted the film and cooled. The resultant was then cut into a rectangle (about 14 cm×10 cm).

TABLE 1

| Component | Example 1 | Example 2 | Example 3 | Example 4 | Comparative Example 1 | Comparative Example 2 | Comparative Example 3 |
|---|---|---|---|---|---|---|---|
| Styrene-isoprene-styrene block copolymer | 20 | 20 | 20 | 20 | 20 | 20 | 20 |
| polyisobutylene | 10 | 10 | 10 | 10 | 10 | 10 | 10 |
| Terpene resin | 20 | 20 | 20 | 20 | 2 | 20 | 20 |
| Liquid paraffin | 47.6 | 45.4 | 44.9 | 38 | 63.4 | 28.2 | 44.9 |
| Isostearic acid | 0.9 | 1.8 | 1.8 | 2.5 | 1.8 | 12 | 1.8 |
| Light anhydrous silicic acid | 0.2 | 0.5 | 0.5 | 1.5 | 0.5 | 7 | 0.5 |
| Dibutylhydroxytoluene | 0.3 | 0.3 | 0.3 | 0.3 | 0.3 | 0.3 | 0.3 |
| Lidocaine | 0.5 | 1.5 | 2 | 7 | 1.5 | 2 | 2 |
| Total | 100 | 100 | 100 | 100 | 100 | 100 | 100 |

The preparations obtained in Examples 1 to 4 and Comparative Examples 1 to 3 were subjected to the following tests.

Adhesive Power Test 180 degree taking off method of Adhesive power test defined in Z0237 of JIS (Japanese Industrial Standards) was done.

As shown in Table 2, example 1 to example 4 (hereinafter referred for present invention) indicate good adhesive power. But, comparative example 1 and comparative example 2 indicate low score. Since the preparation of comparative example 3 is similar to that of the present invention, its adhesive power is good in this test, however the adhesive power of comparative example 3 cannot be maintained in human skin adhesive test described as below.

TABLE 2

| Example 1 | Example 2 | Example 3 | Example 4 | Comparative Example 1 | Comparative Example 2 | Comparative Example 3 |
|---|---|---|---|---|---|---|
| 2.4 | 1.9 | 1.8 | 1.6 | 0.1 | 0.2 | 1.4 |

Human Skin Adhesive Test

The preparation product (14 cm×10 cm/a sheet) were attached to the examinees' back for 12 hours, with the condition of temperature from 25 to 28 degree centigrade, room inside, and no active motion. After 12 hours passed, the approximate area of remaining product on skin was measured as "adhesion remaining ratio".

If the adhesive portion remained curved, the adhesion area was measured by straight line in middle point. The adhesion remaining ratio of the present invention was more than 90%. In comparison, the preparation product of the comparative example 1 and 3 were fully fallen off, and the comparative example 2 was partially fallen off in adhesion test, and most part of comparative example 2 floated off to the skin, as the ratio of adhesion remaining for 14%.

TABLE 3

| Example 1 | Example 2 | Example 3 | Example 4 | Comparative Example 1 | Comparative Example 2 | Comparative Example 3 |
|---|---|---|---|---|---|---|
| 96% | 94% | 96% | 93% | 0% | 14% | 0% |

Drug Remaining Test

As shown in FIG. 1, the preparation product (14 cm×10 cm/a sheet) were attached to the examinees' back for 4 hours, 8 hours, and 12 hours. After each time period was passed, the preparation was removed. The amount of drug remaining in each preparation was measured to determine the drug remaining ratio on the premise that the amount of drug prior to attachment was 100%. In case of the preparation product removed, such removed preparation product was remained on the examinees' back and the examinees are lied down prone with relaxation. Then, the drug remaining test was continued.

The drug remaining ratio after attachment for 12 hours was 96 to 99% in the comparative examples, while the results of all of the present invention products were 80% or less. According to this results, the amount of drug released into the human skin was 20% or more.

The invention claimed is:

1. A non-aqueous patch comprising 0.5 to 7 mass % lidocaine, and a dissolving agent comprising an organic acid and a polyalcohol, wherein the lidocaine and the dissolving agent are in a plaster, the plaster being held by a support, wherein the support has a stretch strength of less than 2,000g/50 mm when the support is stretched by 50% longitudinal extension; and wherein the support comprises a biaxially-oriented stretch cloth, wherein
    the organic acid is isostearic acid, which is present in the plaster in an amount of 0.9 mass % to 2.5 mass %, and
    the polyalcohol is dipropylene glycol, which is present in the plaster in an amount of 0.2 mass % to 1.5 mass % dipropylene glycol.

2. The non-aqueous patch of claim 1, wherein the adhesive power of the patch is from 0.4N/width 25 mm to 5N/width 25 mm.

3. The non-aqueous patch of claim 1, wherein the release ratio of lidocaine from the plaster is more than 6%, after 12 hours attachment to the skin.

4. The non-aqueous patch of claim 1, wherein the amount of lidocaine is 0.1 to 1 mg/cm$^2$ of the plaster.

5. The non-aqueous patch of claim 1, wherein the plaster consists of lidocaine, isostearic acid and dipropylene glycol, an elastomer, a terpene resin, butylated hydroxytoluene, liquid paraffin and light anhydrous silicic acid.

6. The non-aqueous patch of claim 5, wherein
    the elastomer consists of a combination of styrene isoprene and polyisobutylene.

7. The non-aqueous patch of claim 1, wherein the lidocaine is dissolved in the dissolving agent.

8. The non-aqueous patch of claim 5, wherein the lidocaine, the polyalcohol and the organic acid are combined prior to the addition of the elastomer, the terpene resin, the butylated hydroxytoluene, the liquid paraffin and the light anhydrous silicic acid.

* * * * *